United States Patent [19]

Matsuda et al.

[11] 4,236,024

[45] Nov. 25, 1980

[54] PROCESS FOR PRODUCING DIACETOXYBUTENE

[75] Inventors: Teruo Matsuda; Kuniyoshi Manabe, both of Niihama, Japan

[73] Assignee: Sumitomo Chemical Company, Limited, Osaka, Japan

[21] Appl. No.: 15,865

[22] Filed: Feb. 27, 1979

Related U.S. Application Data

[63] Continuation of Ser. No. 807,725, Jun. 17, 1977, abandoned.

[30] Foreign Application Priority Data

Jun. 25, 1976 [JP] Japan .................................. 51-75874
Dec. 29, 1976 [JP] Japan ................................ 51-158918

[51] Int. Cl.³ .......................................... C07C 67/055
[52] U.S. Cl. ..................................... 560/244; 252/439
[58] Field of Search ............... 560/243, 244, 245, 261; 568/857; 252/439

[56] References Cited

U.S. PATENT DOCUMENTS

| 3,221,045 | 11/1965 | McKeon et al. | 560/245 |
| 3,671,577 | 6/1972 | Ono et al. | 560/244 |
| 3,872,163 | 3/1975 | Shimizu et al. | 560/244 |
| 3,922,300 | 11/1975 | Onoda et al. | 560/261 |
| 3,947,495 | 3/1976 | Murib et al. | 562/546 |
| 3,970,697 | 7/1976 | Scheben et al. | 562/548 |

OTHER PUBLICATIONS

Onoda, Takeru et al. "Unsaturated glycol diesters" Japan. Kokai 74-11,812. (See Chemical Abstratcs, Vol. 80 (1974) #145,470q).
Hydrocarbon Processing, Vol. 46(4) pp. 146-149 (1967).

Primary Examiner—Natalie Trousof
Assistant Examiner—L. Hendricksen
Attorney, Agent, or Firm—Wenderoth, Lind & Ponack

[57] ABSTRACT

Diacetoxybutene is prepared in a high yield with a high selectivity from butadiene, acetic acid and oxygen in the presence of a solid catalyst comprising sulfur, at least one noble metal selected from palladium, platinum and rhodium, and a carrier.

9 Claims, No Drawings

PROCESS FOR PRODUCING DIACETOXYBUTENE

This is a continuation of, application Ser. No. 807,725, filed June 17, 1977, now abandoned.

The present invention relates to a method for producing diacetoxybutene from butadiene.

More particularly, it relates to a method for producing diacetoxybutene from acetic acid, molecular oxygen and butadiene using a solid catalyst.

Recently, there is an increasing demand for 1,4-butanediol as an organic solvent and a material for synthetic resins, and as is well known 1,4-butanediol is synthesized by various methods. The well-known industrial method among them is the Reppe reaction in which 1,4-butanediol is synthesized from acetylene and formalin. But, this method has the drawbacks that it requires a complicated reaction process and a high material cost. Another well-known method is one which comprises halogenation of butadiene, hydrolysis of the resulting dihalogenated butene and hydrogenation of the resulting butenediol into the objective butanediol. This method is disadvantageous like the Reppe reaction, in that it requires a complicated reaction process and a high material cost.

At prevent, a method regarded as most important from the industrial point of view is one which comprises oxidizing butadiene in one step in the presence of acetic acid and converting the resulting diacetoxybutene into the objective butanediol through hydrogenation and hydrolysis.

A gas-phase process and a liquid-phase process are proposed for the one-step synthesis of diacetoxybutene from butadiene. In the gas-phase process, by-products are produced in large amounts and the life of the catalyst is short. The liquid-phase process if further classified into two forms depending upon the state of the catalyst in the reaction system. In one form, the catalyst is uniformly in solution in the reaction system. In the other form, the catalyst forms a non-uniform system. In the former process, the separation and recovery of the catalyst are much complicated. The latter process is advantageous in this respect. Various processing using the non-uniform catalyst system are proposed, but they have such drawbacks that the rate of reaction is low, the selectivity of reaction is poor, the cost of catalyst is high and the life of catalyst is short.

One of the latter processes is described in Japanese Patent Kokai (unexamined publication) No. 11,812/1974 in which a catalyst containing palladium and at least one of antimony, bismuth, selenium and tellurium which are supported on a carrier, is used. According to the description of the said Japanese Patent Kokai, the carrier supporting the catalyst is active carbon previously treated with nitric acid, while the activity of the catalyst is relatively lowered without the nitric acid treatment. Japanese Patent Kokai (unexamined publication) No. 140,406/1975 discloses a catalyst containing platinum and at least an element belonging to Group V or VI of Mendelejeff's periodic table (phosphorus, arsenic, bismuth, antimony, selenium and tellurium). But, these catalysts are relatively low in the conversion and selectivity and moreover they are high in cost.

The inventors extensively studied to overcome the said drawbacks and found that diacetoxybutene can be produced in a high yield by reacting acetic acid, a molecular oxygen-containing gas and butadiene in a liquid phase using a solid catalyst comprising sulfur and at least one of palladium, platinum and rhodium, which catalyst may optionally contain another component.

The present invention provides a method for producing diacetoxybutene, which comprises reacting butadiene, acetic acid and an oxygen-containing gas in the presence of a solid catalyst comprising (1) sulfur, (2) at least one noble metal selected from palladium, platinum and rhodium, and (3) a carrier.

In the present invention, the atomic ratio of components supported on the carrier is expressed as follows;

$$Pd_1Pt_{0-10}Rh_{0-10}S_{0.05-10} \tag{1}$$

or $$Pd_{0-10}Pt_1Rh_{0-10}S_{0.05-10} \tag{2}$$

or $$Pd_{0-10}Pt_{0-10}Rh_1S_{0.05-10} \tag{3}$$

The carrier includes alumina, silica alumina, pumice, silica gel, synthetic zeolite, active carbon and the like. Among them, silica gel and active carbon are particularly favorable. Particularly, the active carbon prepared from coal contains sulfur in some amount, so that the active catalyst of the present invention can be prepared by merely adding the above defined noble metal alone or together with another component to the active carbon without addition of fresh sulfur.

The materials or sources for palladium, platinum, rhodium and sulfur, which are a component of the catalyst of this invention, include palladium chloride, palladium nitrate, palladium acetate, chloroplatinic acid, platinum (II) chloride, platinum (IV) chloride, potassium chloroplatinate, rhodium chloride, rhodium nitrate, rhodium sulfate, and sulfur as an element, thiourea, ammonium thiocyanate, sulfur monochloride, and sulfur dichloride as inorganic sulfur, and phenyl sulfide, β-thiodiglycol and dimethyldisulfide as organic sulfur, and an active carbon containing inorganic or organic sulfur.

The catalyst of the present invention may further contain another component. There are exemplified elements belonging to Groups I, IV, V, VI, VII and VIII, the lanthanide group and the actinide group of the said periodic table (e.g. Li, Na, R, Rb, Cs, Cu, Ag, Au, Sn, Pb, Ti, Zr, P, As, Sb, Bi, V, Nb, Ta, Se, Te, Cr, Mo, W, Mn, Re, Fe, Co, Ni, Ru, Ir, La, Ce, Th, U). These elements may be used in the form of oxide, hydroxide, chloride, nitrate, sulfate, carboxylate or the like.

In the preparation of the catalyst of the present invention, at least one of palladium, platinum and rhodium is used in an amount of 0.1 to 30% by weight, preferably 0.2 to 20% by weight, based on the weight of the carrier. When the amount is less than 0.1% by weight, the rate of reaction slows down so much that this process becomes disadvantageous economically. While, when the amount is more than 30% by weight, the amount of by-products produced increases, which is an undesirable tendency.

The amount of sulfur used is 0.05 to 100% by weight, preferably 0.1 to 50% by weight, based on the weight of the carrier. When the amount is less than 0.05% by weight, the rate of reaction slows down so much that this process becomes disadvantageous economically. While, when the amount is more than 100% by weight, the amount of by-products produced undesirably increases.

The amount of the optional component used is up to 50% by weight, preferably 0.1 to 30% by weight, based on the weight of the carrier. An amount of more than 50% by weight is not desirable because the amount of by-products produced increases. The atomic ratio of the optional component with respect to the above said noble metal is up to 10.

Sulfur is first placed on the carrier, for example by dissolving elemental sulfur or a sulfur compound in a suitable solvent, adding the carrier to the solution and drying the solution slowly by evaporation. Thereafter, the above defined noble metal is placed alone or together with the optional component on the dried carrier by mixing the carrier and a solution of the noble metal alone or together with the optional component and drying the solution by evaporation in the same manner as above.

As an alternative to this, it is possible to first place the noble metal or both the noble metal and the optional component on the carrier, and then to place sulfur on the resulting carrier. Further, it is also possible to place all of them on the carrier simultaneously when all of them are soluble in the same solvent.

After at least one noble metal and sulfur, optionally together with the further component, have been placed on the carrier, the whole is dried at 150° to 300° C. and then reduced, for example in a stream of hydrogen or a methanol-saturated vapor, or with a reducing agent such as hydrazine, $NaBH_4$ or formic acid.

The catalyst used in the present invention may have any form depending upon the types of reactor. For example, a fine powder form is desirable when the reaction is carried out according to the slurry process, while a granular form is desirable when the reaction is carried out according to the fluidized bed process.

The amount of catalyst used in the reaction between butadiene, acetic acid and molecular oxygen is 0.2 to 30% by weight, preferably 0.5 to 20% by weight, based on the total weight of butadiene and acetic acid. When the amount is less than 0.2% by weight, the rate of reaction slows down so much that this process becomes disadvantageous industrially. When the amount is more than 30% by weight, the amount of by-products produced increases undesirably.

The amount of acetic acid used is 2 to 100 moles, preferably 5 to 50 moles, per mole of butadiene used. When the molar ratio is less than 2, the rate of reaction slows down and at the same time the selectivity extremely drops. While, when the molar ratio is more than 100, the separation of the objective product after the reaction is uneconomical operationally so that this process becomes disadvantageous industrially.

The oxygen-containing gas used in the present invention includes a pure oxygen and an oxygen gas diluted with an inert gas, such as air. The amount of oxygen used is stoichiometric or more, in other words, 0.5 mole or more per mole of butadiene.

The concentration of oxygen in the reactor is not particularly limited, so long as the concentration in the gaseous phase is outside the explosion limits. The reaction temperature is 30° to 200° C., preferably 50° to 150° C. A temperature of lower than 30° C. is uneconomical, because the rate of reaction extremely slows down. A temperature of higher than 200° C. is also undesirable because the selectivity to diacetoxybutenes becomes very poor.

The reaction pressure is atmospheric pressure to 200 atm., preferably atmospheric pressure to 100 atm. A pressure of higher than 200 atm. is not desirable in terms of safety and economy of equipment.

The present invention will be illustrated with reference to the following examples, but the present invention is not limited to these examples.

In the examples, the conversion of butadiene is expressed in mole % of butadiene consumed to the total butadiene used, the yield of diacetoxybutenes is expressed in mole % of diacetoxybutenes produced in the total butadiene used, and the selectivity to diacetoxybutenes is expressed in a percentage of the yield of diacetoxybutenes to the conversion of butadiene.

EXAMPLE 1

0.67 g. (5 m.mole) of sulfur chloride was dissolved in 20 ml of carbon disulfide, and 5.0 g. of active carbon (made from coconut) containing 0.03% by weight of sulfur was added thereto. The solution was then dried gradually by evaporation on a water bath. Thereafter, the dried product was placed in 20 ml of 5 N hydrochloric acid solution containing 0.44 g. (2.5 m.mole) of palladium chloride and the solution was then dried gradually by evaporation on a water bath. The dried product was packed in a combustion tube, dried at 150° C. for 2 hours in the stream of nitrogen, reduced at 200° C. for 2 hours with a methanol-nitrogen mixed gas (nitrogen gas saturated with methanol at room temperature) and then further reduced at 400° C. for 1 hour.

0.10 g. of the catalyst thus obtained was placed in a 25-ml glass tube, and 4.2 g. (70 m.mole) of acetic acid was added thereto. The glass tube was cooled to −70° C. in a dry ice-methanol bath, and 0.108 g. (2 m.mole) of butadiene was added thereto. The atmosphere of the glass tube was replaced with pure oxygen, and the tube was then sealed by means of a burner.

Reaction was carried out for 2 hours while rotating the sealed glass tube in a water bath of 85° C. The reaction liquor was analyzed by gas-chromatography and it was found that the conversion of butadiene was 42.95%, the yield of diacetoxybutenes was 36.0% and the selectivity to diacetoxybutenes was 83.9%.

EXAMPLE 2

5.0 g. of active carbon (made from bituminous coal) containing 0.25% by weight of sulfur was placed in 20 ml of 5 N hydrochloric acid solution containing 0.44 g. (2.5 m.mole) of palladium chloride.

The solution was then gradually dried by evaporation on a water bath. The dried product was treated in the same manner as in Example 1 and used for the reaction. The reaction liquor produced was analyzed by gas-chromatography and it was found that the conversion of butadiene was 33.3%, the yield of diacetoxybutene was 24.0% and the selectivity to diacetoxybutenes was 72.1%.

EXAMPLE 3

0.67 g. (5 m.mole) of sulfur chloride was dissolved in 20 ml of carbon disulfide, and 5.0 g. of the same active carbon as in Example 2 containing 0.25% by weight of sulfur was added thereto. The solution was then gradually dried by evaporation on a water bath. The dried product was treated in the same manner as in Example 1 and used for the reaction. The reaction liquor obtained was analyzed by gas-chromatography and it was found that the conversion of butadiene was 60.0%, the yield of diacetoxybutenes was 52.8% and the selectivity to diacetoxybutenes was 88.0%.

EXAMPLE 4

0.04 g. (1.25 m.mole) of sulfur powder was dissolved in 20 ml of carbon disulfide, and 5.0 g. of active carbon (made from coconut) containing 0.03% by weight of sulfur was added thereto. The solution was then gradually dried by evaporation on a water bath. The dried product was placed in 20 ml of 5 N hydrochloric acid solution containing 0.65 g. (1.25 m.mole) of chloroplatinic acid. The solution was then gradually dried by evaporation on a water bath. The dried product was treated in the same manner as in Example 1 and used for the reaction. The reaction liquor produced was analyzed by gas-chromatography and it was found that the conversion of butadiene was 8.1%, the yield of diacetoxybutenes was 6.5% and the selectivity to diacetoxybutenes was 80.2%.

EXAMPLE 5

0.08 g. (2.5 m.mole) of sulfur powder was dissolved in 20 ml of carbon disulfide, and 5.0 g. of active carbon (made from coconut) containing 0.03% by weight of sulfur was added thereto. The solution was then gradually dried by evaporation on a water bath. Thereafter, the dried product was placed in 20 ml of 5 N hydrochloric acid solution containing 0.66 g. (2.5 m.mole) of rhodium chloride trihydrate. The solution was then gradually dried by evaporation on a water bath.

The dried product thus obtained was then treated in the same manner as in Example 1 and used for the reaction. The reaction liquor produced was analyzed by gas-chromatography and it was found that the conversion of butadiene was 12.4%, the yield of diacetoxybutenes was 9.4% and the selectivity to diacetoxybutenes was 75.8%.

EXAMPLE 6

0.67 g. (5 m.mole) of sulfur chloride was dissolved in 20 of carbon disulfide, and 5.0 g. of active carbon (made from bituminous coal) containing 0.25% by weight of sulfur was added thereto. The solution was then gradually dried by evaporation on a water bath. The dried product was placed in 20 ml of 5 N hydrochloric acid solution containing 0.22 g. (1.25 m.mole) of palladium chloride and 0.325 g. (0.625 m.mole) of chloroplatinic acid. The solution was then gradually dried by evaporation on a water bath. The dried product thus obtained was then treated in the same manner as in Example 1 and used for the reaction. The reaction liquor produced was analyzed by gas-chromatography and it was found that the conversion of butadiene was 62.0%, the yield of diacetoxybutene was 54.0% and the selectivity to diacetoxybutene was 87.1%.

EXAMPLE 7

0.67 g. (5 m.mole) of sulfur chloride was dissolved in 20 ml of carbon disulfide, and 5.0 g. of active carbon (made from bituminous coal) containing 0.25% by weight of sulfur was added thereto. The solution was then gradually dried by evaporation on a water bath. The dried product was placed in 20 ml of 5 N hydrochloric acid solution containing 0.22 g. (1.25 m.mole) of palladium chloride, 0.325 g. (0.625 m.mole) of chloroplatinic acid and 0.165 g. (0.625 m.mole) of rhodium chloride trihydrate. The solution was then gradually dried by evaporation on a water bath. The dried product thus obtained was then treated in the same manner as in Example 1 and used for the reaction. The reaction liquor produced was analyzed by gas-chromatography and it was found that the conversion of butadiene was 68%, the yield of diacetoxybutenes was 60.2% and the selectivity to diacetoxybutenes was 88.5%.

EXAMPLE 8

The 0.67 g. (5 m.mole) of sulfur chloride was dissolved in 20 ml of carbon disulfide, and 5.0 g. of active carbon (made from bituminous coal) containing 0.95% by weight of sulfur was added thereto. After the active carbon was dipped in the solution for 1 hour, the solution was gradually dried by evaporation on a wather bath.

The dried product was placed in 20 ml of 5 N hydrochloric acid solution containing 0.44 g. (2.5 m.mole) of palladium chloride and 0.075 g. (0.2 m.mole) of lead acetate. The solution was then gradually dried by evaporation on a water bath. The dried product was treated in the same manner as in Example 1 and used for the reaction. It was found by analysis that the conversion of butadiene was 85.0%, the yield of diacetoxybutenes was 77.0% and the selectivity to diacetoxybutenes was 90.6%.

EXAMPLE 9

0.67 g. (5 m.mole) of sulfur chloride was dissolved in 20 ml of carbon disulfide, and 5.0 g. of active carbon (made from bituminous coal) containing 0.95% by weight of sulfur was added thereto. After the active carbon was dipped in the solution for 1 hour, the solution was gradually dried by evaporation on a water bath.

The dried product was placed in 20 ml of 5 N hydrochloric acid solution containing 0.44 g. (2.5 m.mole) of palladium chloride. The solution was then gradually dried by evaporation on a water bath.

Thereafter, the dried product was placed in 20 ml of an ethanol solution containing 0.044 g. (0.2 m.mole) of stannous chloride. The solution was then gradually dried by evaporation on a water bath.

The dried product thus obtained was treated in the same manner as in Example 1 and used for the reaction. It was found by analysis that the conversion of butadiene was 90.0%, the yield of diacetoxybutenes was 81.5% and the selectivity to diacetoxybutenes was 90.5%.

EXAMPLES 10 TO 17

The preparation of catalyst and the reaction were carried out in completely the same manner as in Example 8 except that lead acetate was replaced with the metal salts described below. The results are shown in the following table.

Example 10: 0.044 g. (0.2 m.mole) of antimony trichloride
Example 11: 0.032 g. (0.2 m.mole) of tellurium dioxide
Example 12: 0.044 g. (0.2 m.mole) of ruthenium trichloride
Example 13: 0.10 g. (0.2 m.mole) of uranium nitrate
Example 14: 0.084 g. (0.2 m.mole) of chloroauric acid
Example 15: 0.04 g. (0.2 m.mole) of manganese chloride
Example 16: 0.088 g. (0.2 m.mole) of cerous nitrate
Example 17: 0.054 g. (0.2 m.mole) of niobium pentachloride

TABLE

| Example | Sulfur content in active carbon (% by weight) | Metal supported* (m.mole) | | | | Conversion of butadiene (%) | Yield of diacetoxybutenes (%) | Selectivity to diacetoxybutenes (%) |
| --- | --- | --- | --- | --- | --- | --- | --- | --- |
| | | Pd | S | metal | added | | | |
| 10 | 0.95 | 2.5 | 5 | Sb | 0.2 | 82.0 | 74.0 | 90.3 |
| 11 | " | " | " | Te | 0.2 | 70.0 | 63.7 | 91.0 |
| 12 | " | " | " | Ru | 0.2 | 65.0 | 60.5 | 93.0 |
| 13 | " | " | " | U  | 0.2 | 81.0 | 73.7 | 91.0 |
| 14 | " | " | " | Au | 0.2 | 82.0 | 74.0 | 90.2 |
| 15 | " | " | " | Mn | 0.2 | 78.0 | 70.6 | 90.5 |
| 16 | " | " | " | Ce | 0.2 | 76.0 | 67.6 | 89.0 |
| 17 | " | " | " | Nb | 0.2 | 88.0 | 81.0 | 92.0 |

Note:
*The mole number of the metal added to 5 g. of active carbon in the preparation of catalyst.

EXAMPLE 18

0.67 g. (5 m.mole) of sulfur chloride was dissolved in 20 ml of acetone and 5.0 g. of active carbon (made from bituminous coal) containing 0.95% by weight of sulfur was added thereto. After the active carbon was dipped in the solution for 1 hour, the solution was gradually dried by evaporation on a water bath.

The dried product was placed in 20 ml. of water and allowed to stand for about 30 minutes thereby to hydrolyze the adsorbed sulfur chloride. The liquor was then gradually dried by evaporation on a water bath.

The dried product was placed in 20 ml of an ethyl alcohol solution containing 0.072 g. (0.2 m.mole) of tantalum pentachloride. The solution was then gradually dried by evaporation on a water bath.

Next, the dried product was placed in 20 ml of 5 N hydrochloric acid solution containing 0.44 g. (2.5 m.mole) of palladium chloride. The solution was then gradually dried by evaporation on a water bath.

The dried product thus finally obtained was treated in the same manner as in Example 1 and used for the reaction. It was found by analysis that the conversion of butadiene was 85.5%, the yield of diacetoxybutenes was 79.9% and the selectivity to diacetoxybutenes was 93.5%.

What is claimed is:

1. A method for producing diacetoxybutene, which comprises reacting butadiene, acetic acid and an oxygen-containing gas, in a liquid phase, in the presence of a solid catalyst comprising a catalyst system supported on a carrier, the components of the catalyst system and their atomic ratios being represented by the formula:

$$Pd_1Pt_{0-10}Rh_{0-10}S_{0.05-10} \quad (1)$$

or $$Pd_{0-10}Pt_1Rh_{0-10}S_{0.05-10} \quad (2)$$

or $$Pd_{0-10}Pt_{0-10}Rh_1S_{0.05-10} \quad (3).$$

2. A method according to claim 1, wherein the solid catalyst also comprises at least one further member selected from elements belonging to Groups I, IV, V, VI, VII and VIII, and elements belonging to the Lanthanide and Actinide Groups, of Mendelejeff's periodic table.

3. A method according to claim 1, wherein the reaction is carried out at a temperature of 30° to 200° C.

4. A method according to claim 1, wherein the reaction is carried out at a pressure of atmosphere pressuric to 200 atm.

5. A method according to claim 1, wherein the molar ratio of acetic acid to butadiene is 2–100:1.

6. A method according to claim 2, wherein the amount of the further member is up to 50% by weight, based on the weight of the carrier.

7. A method according to claim 1, wherein the total amount of the Pd, Pt and Rh in the catalyst system is 0.1 to 30% by weight based on the weight of the carrier, and the amount of the S in the catalyst system is 0.05 to 100% by weight based on the weight of the carrier.

8. A method according to claim 1, wherein the carrier is alumina, silica alumina, pumice, silica gel, synthetic zeolite or active carbon.

9. A method according to claim 1, wherein the amount of the solid catalyst is 0.2 to 30% by weight, based on the total weight of the butadiene and acetic acid.

* * * * *